United States Patent
Yamasaki et al.

(10) Patent No.: US 8,568,746 B2
(45) Date of Patent: Oct. 29, 2013

(54) TRANSDERMAL COMPOSITION OF PHOSPHATIDYLCHOLINE AND METHOD FOR PRODUCING SAME

(75) Inventors: Keiko Yamasaki, Higashikagawa (JP); Takahiro Tanimoto, Higashikagawa (JP)

(73) Assignee: MEDRx Co., Ltd., Kagawa (JP)

(*) Notice: Subject to any disclaimer, the term of this patent is extended or adjusted under 35 U.S.C. 154(b) by 123 days.

(21) Appl. No.: 13/392,181

(22) PCT Filed: May 21, 2010

(86) PCT No.: PCT/JP2010/003447
§ 371 (c)(1),
(2), (4) Date: Feb. 24, 2012

(87) PCT Pub. No.: WO2011/024354
PCT Pub. Date: Mar. 3, 2011

(65) Prior Publication Data
US 2012/0149664 A1  Jun. 14, 2012

(30) Foreign Application Priority Data

Aug. 25, 2009  (JP) ................ 2009-193858

(51) Int. Cl.
*A61K 9/00* (2006.01)
*A61K 8/02* (2006.01)
*A61K 9/70* (2006.01)
*A61F 13/00* (2006.01)

(52) U.S. Cl.
USPC ............ 424/400; 424/401; 424/449

(58) Field of Classification Search
None
See application file for complete search history.

(56) References Cited

U.S. PATENT DOCUMENTS

2005/0208012 A1  9/2005  Albrecht et al.
2007/0243211 A1* 10/2007 Jaffe ............. 424/195.17
2009/0196914 A1*  8/2009  Hofland ............. 424/450

FOREIGN PATENT DOCUMENTS

| JP | 2001-151624 A | 6/2001 |
| JP | 2002-226402 A | 8/2002 |
| JP | 2007-509085 A | 4/2007 |
| JP | 2007-515439 A | 6/2007 |
| JP | 2008-189219 A | 7/2008 |
| JP | 2009-514965 A | 4/2009 |
| WO | 01/82878 A1 | 11/2001 |

OTHER PUBLICATIONS

Phospholipon(R) 90H product detail accessed online at http://www.lipoid.com on Oct. 30, 2012 and Nov. 5, 2012.*

* cited by examiner

*Primary Examiner* — Carlos Azpuru
*Assistant Examiner* — Casey Hagopian
(74) *Attorney, Agent, or Firm* — Morgan, Lewis & Bockius LLP

(57) ABSTRACT

Disclosed is a transdermal composition, which uses high-purity phosphatidylcholine that is most susceptible to oxidation and the like, and which exhibits high stability and high migration into the skin. Specifically, a transdermal composition having good stability and migration into the skin is able to be obtained by preparing a transdermal composition (a colloidal dispersion liquid of phosphatidylcholine) that contains high-purity phosphatidylcholine, carnitine, a polyhydric alcohol and water. Since the transdermal composition does not contain an oleaginous base (an oil component), the transdermal composition has skin compatibility and is thus useful as a therapeutic agent or a cosmetic preparation. In addition, phosphatidylcholine and carnitine have an effect of achieving good migration into the skin and are capable of promoting systemic or local lipid metabolism in subcutaneous adipose tissues. Consequently, the transdermal composition is able to provide a transdermal preparation that is capable of promoting lipolysis in subcutaneous adipose tissues.

14 Claims, 2 Drawing Sheets

TRANSDERMAL COMPOSITION OF PHOSPHATIDYLCHOLINE AND METHOD FOR PRODUCING SAME

The present application is a U.S. National Phase Application of International Application No. PCT/JP2010/003447, filed May 21, 2010, which claims the benefit of priority of Japanese Application No. 2009-193858 filed Aug. 25, 2009, the disclosures of which are incorporated herein by reference in their entireties.

TECHNICAL FIELD

The present invention relates to a composition for transdermal administration, which enables phosphatidylcholine to be stable in an aqueous liquid and enables phosphatidylcholine to be highly absorbed in the skin.

BACKGROUND ART

The subcutaneous accumulation of fat is correlated with the impaired function of fat cells; fat cells contain fats in the forms of free fatty acid and triglyceride. Triglyceride, which has been formed and accumulated in the fat cells, is also again decomposed to fatty acid, glycerol, and/or glycerol ester by enzymatic degradation. However, when significant imbalance between fat formation and fat decomposition occurs in the body due to various reasons (e.g. poor hormonal function, too abundant diet, inactivation, and aging), triglyceride accumulates in fat cells, resulting in subcutaneous accumulation of fat. Consequently, overweight and therapeutic/cosmetic problems arise.

A method, where a composition which removes the subcutaneous accumulation of fat is directly injected under the skin, has been applied to the treatment of subcutaneous fat accumulation or an obesity accompanied by an excessive fat layer. A phosphatidylcholine preparation represented by Lipostabil (Sanofi-Aventis) is used for that purpose (Patent Literatures 2 and 3). However, the method has raised questions about safety as well as pain during operation, and the method can be said to be a high-risk method. In addition, in the production process of the preparation used for the method, phosphatidylcholine is dissolved together with a solubilizer (bile acid) in an organic solvent, and after concentration and drying, it is dispersed in water to provide a liposome under high pressure. Thus, the process requires a complex and advanced technology as well as great expense. Further, the transdermal administration of the composition also requires a physical auxiliary operation such as iontophoresis.

On the other hand, phosphatidylcholine is widely used as an emulsifier for medicinal products or cosmetics. However, temporal stability is also an important issue in that case (Patent Literature 1).

In addition, there has been growing demand for weight loss from the viewpoint of beauty as well as obesity accompanied by an excessive fat layer, and phosphatidylcholine derivative is also used for that purpose. However, a preparation for transdermal administration of phosphatidylcholine which allows self-administration, has not been found.

CITATION LIST

Patent Literature

Patent Literature 1: JP-A-2001-151624
Patent Literature 2: JP-A-2007-509085
Patent Literature 3: JP-A-2007-515439

SUMMARY OF INVENTION

Problem to be Solved by the Invention

An object of the present invention is to produce a high-purity phosphatidylcholine transdermal preparation. Examples of the phosphatidylcholine include egg yolk- or soybean-derived phosphatidylcholine, hydrogenated phosphatidylcholine, and lysophosphatidylcholine. Considering the skin safety etc. when phosphatidylcholine is administered at a high concentration or for a long period as a transdermal preparation, a natural product-derived high-purity phosphatidylcholine containing minimized impurities is selected. However, the fatty acid of a high-purity phosphatidylcholine has a high iodine value and is considered to be susceptible to oxidation and the like. Accordingly, it has been an important problem to be solved how the stability and transdermal absorbability of the high-purity phosphatidylcholine are secured.

Solution to the Problem

To secure the stability of high-purity phosphatidylcholine, the present inventors have studied on preparation of a homogeneous solution of phosphatidylcholine. Firstly, the inventors found that selection of polyalcohol as a solubilizer for phosphatidylcholine allows a homogeneous solution of phosphatidylcholine. Namely, it has been found that the use of a mixture of, for example, propylene glycol and glycerin, as polyalcohol, enables preparation of a homogeneous solution of phosphatidylcholine; and the homogeneous solution can be prepared at a temperature of 40° C. or lower so that heating is not needed.

As the result of intensive studies for stabilizing phosphatidylcholine, the inventors further found that when an aqueous solution of L-carnitine, which is a substance seen in a living body and involved in lipid metabolism like the phosphatidylcholine and has an amphoteric ion pair in the molecule like the phosphatidylcholine, is homogeneously dispersed in a mixture of phosphatidylcholine and propylene glycol/glycerin, the stability of phosphatidylcholine can be markedly improved without using an antioxidant or a surfactant, and at the same time, the transdermal absorption of phosphatidylcholine is markedly improved. For the reason of this effect, the inventors considered that a cluster ion of the phosphatidylcholine and the carnitine is formed in the solution, and the influence of the cluster ion has resulted in providing the above effect. Accordingly, as a result of intensive studies, the inventors have found that a smaller average diameter of colloidal particles of about 100 nm or less allows the transdermal absorption of phosphatidylcholine to be better.

The composition of the present invention is prepared by only a hydrophilic solvent and a hydrophilic solute and an oil component or a surfactant is not used. Thus, the resultant composition is kind to the skin and adaptable to the skin. Moreover, the method of preparing the composition is very simple because the preparation is completed by only a single mixing step at low temperature.

In addition, the blend of the phosphatidylcholine and L-carnitine can be expected to exert a synergistic effect on weight loss.

The present inventors have accomplished the present invention based on the above findings.

The summary of the present invention is described as follows.

(1) A transdermal composition comprising phosphatidylcholine, carnitine, polyalcohol and water.

(2) The transdermal composition according to (1), wherein the phosphatidylcholine is at least one selected from the group consisting of egg yolk phosphatidylcholine, hydrogenated egg yolk phosphatidylcholine, egg yolk lysophosphatidylcholine, soybean phosphatidylcholine, hydrogenated soybean phosphatidylcholine and soybean lysophosphatidylcholine.

(3) The transdermal composition according to (1), wherein the phosphatidylcholine is egg yolk high-purity phosphatidylcholine.

(4) The transdermal composition according to (1) to (3), wherein the carnitine is L-carnitine.

(5) The transdermal composition according to any of (1) to (4), wherein the polyalcohol is dihydric alcohol, trihydric alcohol or a mixture thereof.

(6) The transdermal composition according to (5), wherein the dihydric alcohol is propylene glycol.

(7) The transdermal composition according to (5), wherein the trihydric alcohol is glycerin.

(8) The transdermal composition according to any of (1) to (5), wherein the polyalcohol contains 0.2 to 3 parts by weight of glycerin per 1 part by weight of propylene glycol.

(9) The transdermal composition according to any of (1) to (8), wherein the phosphatidylcholine is homogeneously dispersed in the composition.

(10) The transdermal composition according to any of (1) to (8), wherein the phosphatidylcholine and the carnitine are homogeneously dispersed in the composition.

(11) The transdermal composition according to any of (1) to (10), wherein the homogeneous dispersion is colloidal dispersion and shows a Tyndall phenomenon.

(12) The transdermal composition according to any of (1) to (11), wherein the colloids in the colloidal dispersion have a particle diameter of 1 μm or less.

(13) The transdermal composition according to any of (1) to (12), wherein the transdermal composition is a liquid consisting of a hydrophilic base.

(14) The transdermal composition according to any of (1) to 13), wherein the total content of phosphatidylcholine and L-carnitine is 1 to 16 w/w %.

(15) The transdermal composition according to any of (1) to (14), wherein the content of L-carnitine relative to the phosphatidylcholine is 0.1 to 5 parts by weight of the carnitine per 1 part by weight of the phosphatidylcholine.

(16) The transdermal composition according to any of (1) to (15), wherein the content of L-carnitine relative to the phosphatidylcholine is 1 to 15-fold moles per 1 mole of the phosphatidylcholine.

(17) The transdermal composition according to any of (1) to (16), further comprising a preservative.

(18) The transdermal composition according to any of (1) to (17), further comprising a fragrance.

(19) The transdermal composition according to any of (1) to (18), wherein the fragrance is ethanol.

(20) The transdermal composition according to any of (1) to (19), wherein the property (pH) of the liquid of the composition is 5 to 7.

Effects of Invention

The composition of the present invention is a transdermal absorption type preparation in which a phosphatidylcholine is stably dispersed as colloidal particles in a solution consisting of a hydrophilic base and which can be self-administered. Thus, it can be suitably used as a transdermal preparation for external use and a cosmetic for removing or reducing the subcutaneous accumulation of fat at a desired site. In addition, because the composition is prepared by only a hydrophilic solvent and a hydrophilic solute without using an oil component or a surfactant, the production of the composition is completed by only a single mixing step and the resultant composition is kind to the skin and adaptable to the skin.

DESCRIPTION OF EMBODIMENTS

—First Aspect of Present Invention—

Figure 2:
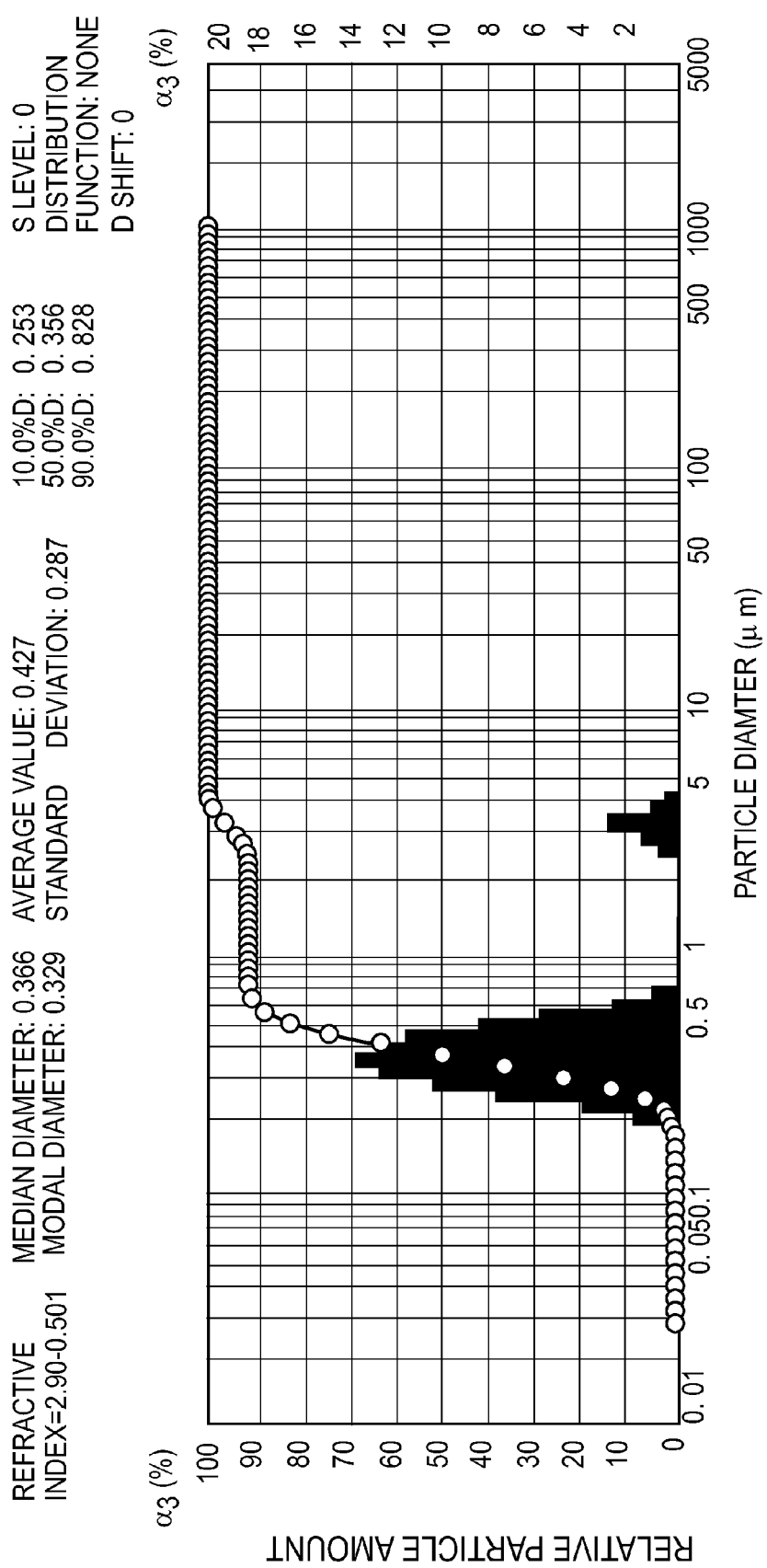
FIG. 2 is a graph showing the particle diameter of colloidal particles in the external composition of sample No. 2 of Example 1.

A first aspect of the present invention relates to a transdermal composition comprising phosphatidylcholine, carnitine, polyalcohol, and water, and relates to a transdermal composition comprising no oily base (lipophilic base). The transdermal composition is adaptable to the skin because it comprises no oily base (oil component). The transdermal composition of the present invention is also a dispersion having a high degree of transparency and showing a clear Tyndall phenomenon, and the average particle diameter (d50) has been 1 μm or less as measured using a laser diffraction particle size distribution analyzer (SALD-2200 from Shimadzu Corporation) as shown in FIG. 2. This colloidal dispersion system is stable, and the time-dependent aggregation and the like have not been observed.

The colloidal particles of the present invention have an average particle diameter of about 0.05 μm or more, preferably 0.5 μm or less. More preferably, the average particle diameter may be 0.05 to 0.4 μm.

The phosphatidylcholine of the present invention may be used by selecting at least one from the group consisting of egg yolk phosphatidylcholine, hydrogenated egg yolk phosphatidylcholine, egg yolk lysophosphatidylcholine, soybean phosphatidylcholine, hydrogenated soybean phosphatidylcholine, and soybean lysophosphatidylcholine. Preferably, the phosphatidylcholine may be egg yolk high-purity phosphatidylcholine. The concentration of the phosphatidylcholine in the composition is preferably 0.5 to 8% by weight, more preferably 1 to 6% by weight, still more preferably 1 to 4% by weight.

The carnitine of the present invention refers to DL-carnitine, L-carnitine, or acetyl-L-carnitine. Preferably, the carnitine may be L-carnitine. The carnitine may be used in any of the forms of an intramolecular salt, a hydrochloride, an inorganic salt such as a sodium salt, and an organic salt such as an oxalate, a tartrate, and a fumarate.

The amount of carnitine added to phosphatidylcholine is preferably 0.1 to 5 parts by weight, more preferably 0.5 to 3 parts by weight of carnitine per 1 part by weight of phosphatidylcholine.

The total content of the phosphatidylcholine and the carnitine according to the present invention is preferably 1 to 16% by weight.

With regard to the molecular weight of the phosphatidylcholine of the present invention, for example, egg yolk high-purity phosphatidylcholine, which comprises mainly 4 types of phosphatidylcholine having fatty acids of different lengths, has molecular weight distributed from about 730 to 790. Because the molecular weight of L-carnitine is 161.2, the desirable molar ratio of L-carnitine to the phosphatidylcholine is about 2 to about 15 assuming that the value of the phosphatidylcholine is 1. It is preferably about 4 to about 10 assuming that the value of the phosphatidylcholine is 1.

In general, fatty acids of phosphatidylcholine (carbon number 16 to 18) tend to form micelles by the association of the fatty acids. However, it is probable that the addition of L-carnitine results in the formation of a cluster ion with the phosphatidylcholine to suppress the formation of micelles. As a result, the formed phosphatidylcholine micelles have been found to be gradually subdivided and the degree of transparency of the solution is improved over time. The above results have showed that colloidal particles, resulting from the cluster ion mainly comprising the phosphatidylcholine and the carnitine, are formed in the solution.

Examples of the polyalcohol of the present invention can include alcohols each having 2 hydroxyl groups, such as propylene glycol, 1,3-butanediol, and polyethylene glycol; alcohols each having 3 hydroxyl groups, such as glycerin; saccharides such as glucose, fructose, lactose, and trehalose; and mixtures thereof.

Preferred examples of the polyalcohol can include a mixture of an alcohol having 2 hydroxyl groups and an alcohol having 3 hydroxyl groups. For example, a mixture of propylene glycol and glycerin or the like is preferable.

When the polyalcohol is a mixture, for example, the mixing ratio of propylene glycol to glycerin is preferably 0.2 to 3 parts by weight of glycerin per 1 part by weight of propylene glycol. It is more preferably 0.5 to 1.5 parts by weight of glycerin per 1 part by weight of propylene glycol. A different polyalcohol may be added to the mixture of propylene glycol and glycerin. However, it is necessary that adequate caution is exercised in the substitute of propylene glycol. For example, the use of polyethylene glycol 400 as a substitute for propylene glycol easily causes liquid phase separation in the polyalcohol solution, and the use of 1,3-butanediol as a substitute for propylene glycol easily causes a liquid to have white turbidity owing to the insolubilization of the phosphatidylcholine.

—Second Aspect of Present Invention—

The present invention relates to a method for producing a transdermal composition comprising a phosphatidylcholine. Namely, it relates to a method for producing a dispersion liquid of colloid which is a cluster ion of a phosphatidylcholine and L-carnitine, characterized in that the dispersion is obtained by homogeneously dispersing an aqueous solution of the carnitine in a polyalcohol solution of the phosphatidylcholine.

As the "polyalcohol" of the present invention, preferably, a mixture of a dihydric alcohol and a trihydric alcohol may be used. For example, a polyalcohol solution of the phosphatidylcholine can be produced using a mixture of, for example, propylene glycol and glycerin, and egg yolk-derived high-purity phosphatidylcholine as a phosphatidylcholine.

The concentration of the phosphatidylcholine in the polyalcohol solution is preferably 1 to 16% by weight, more preferably 2 to 12% by weight.

The concentration of L-carnitine in the "L-carnitine aqueous solution" of the present invention may be 0.2 to 16% by weight, preferably 0.5 to 12% by weight. The L-carnitine aqueous solution used to be added and dispersed in the polyalcohol solution of the phosphatidylcholine is preferably added so that the amount of L-carnitine is 0.1 to 3 parts by weight per 1 part by weight of the phosphatidylcholine. More preferably, the L-carnitine aqueous solution may be added so that the amount of L-carnitine is 0.25 to 2 parts by weight.

The pH of the L-carnitine aqueous solution used in the present invention is preferably 5 to 8 and more preferably, the pH may be 6 to 7. Any of an organic acid and an inorganic acid may be used as a pH adjuster. When the inorganic acid is used alone, the amount of its use needs to be reduced to a small amount because aggregation might occur over time. Examples of the organic acid include acetic acid, citric acid, tartaric acid, and malic acid. Examples of the inorganic acid include hydrochloric acid and phosphoric acid. Preferably, the pH adjuster may be an organic acid, and preferred examples of the organic acid include citric acid and tartaric acid. The liquid property (pH) of the transdermal composition prepared by using the L-carnitine aqueous solution is preferably about 5 to 8, and more preferably the pH may be 5 to 6. Still more preferably, the pH may be around about 5.

The "dispersing an L-carnitine aqueous solution in a polyalcohol solution of a phosphatidylcholine" according to the present invention refers to homogeneously dispersing the L-carnitine aqueous solution in the polyalcohol solution to give a composition comprising a cluster ion of the phosphatidylcholine and the carnitine. In a conventional method for producing the aqueous dispersion, the polyalcohol solution is put by drops to the aqueous solution. Thus, the process employed in the present invention is opposite to the conventional method. For example, according to the conventional method, the polyalcohol solution of the phosphatidylcholine was dispersed in the L-carnitine aqueous solution to prepare a colloidal dispersion composition. However, the resulting colloidal dispersion composition was not a desired transdermal composition in which colloids of a particle diameter as provided according to the present invention were dispersed and stabilized.

A stirrer may be used to homogeneously disperse the L-carnitine aqueous solution in the polyalcohol solution. The speed of rotation is preferably 50 to 3,000 rotations per minute. More preferably, the speed of rotation may be 100 to 1,000 revolutions per minute.

In addition, depending on a particular object, various reagents used for external preparations or cosmetics may be added to the transdermal composition of the present invention. Examples of various reagents which may be added include a fragrance, an antioxidant, a preservative, a colorant, a buffer, and a pH adjuster. For example, as the fragrance, for example, ethanol, or orange essence may be used; as the antioxidant, for example, tocopherol acetate, sodium edetate, erythorbic acid, or 1,3-butylene glycol may be used; and as the preservative, for example, sorbic acid and taurine may be used. Examples of the pH adjuster include an organic acid such citric acid, acetic acid, or tartaric acid and an inorganic acid such as phosphoric acid or hydrochloric acid.

Further, an ultraviolet absorber and an antimicrobial agent may be added depending on a particular object.

EXAMPLES

The present invention will be described below in detail with reference to Examples. However, it is to be understood that the present invention is not limited to these Examples.

Example 1

Preparation of External, Composition Comprising Egg Yolk High-Purity Phosphatidylcholine and L-Carnitine Each reagent was weighed to prepare each of the composition having a composition ratio (w/w %) as listed in Table 1 below. Firstly, propylene glycol and glycerin were added to an egg yolk high-purity phosphatidylcholine, and were dissolved while stirring. Then, an L-carnitine aqueous solution was added to the resulting solution, and dispersed while stirring to give each transdermal composition listed in Table 1. A pH adjuster was added in such an appropriate amount as to provide a pH of 5.

However, as shown in Table 1, in the case of the Nos. 1 to 4 of the present invention containing L-carnitine, 40 to 50% of the phosphatidylcholine and L-carnitine administered were found to be absorbed into the skin. The transdermal absorptions of phosphatidylcholine and L-carnitine are shown to be

TABLE 1

| Reagent | Reference Example 1 | Reference Example 2 | No. 1 | No. 2 | No. 3 | No. 4 |
|---|---|---|---|---|---|---|
| Egg Yolk High-Purity Phosphatidylcholine (Mw 732~790) | 2.0 (2.5-2.7 mM) | 2.0 (2.5-2.7 mM) | 2.0 (2.5-2.7 mM) | 2.0 (2.5-2.7 mM) | 2.0 (2.5-2.7 mM) | 2.0 (2.5-2.7 mM) |
| L-Carnitine (Mw 161.2) | — | — | 1.0 (6.2 mM) | 2.0 (12.4 mM) | 3.0 (18.6 mM) | 4.0 (24.8 mM) |
| Propylene Glycol | 23 | 23 | 23 | 22 | 23 | 26 |
| Glycerin | 23 | 23 | 23 | 22 | 20 | 22 |
| Tocopherol Acetate | — | 1.0 | — | — | — | — |
| Water | 44 | 43 | 46 | 43 | 43 | 38 |
| Ethanol | 8 | 8 | 9 | 9 | 9 | 8 |
| pH Adjuster (Citric Acid) | — | — | Appropriate Amount | Appropriate Amount | Appropriate Amount | Appropriate Amount |
| Property of liquid (pH) | 5 | 5 | 5 | 5 | 5 | 5 |

[Note]
— represents no addition.

Using each transdermal composition listed in Table 1, a stability test for the phosphatidylcholine (the measurement of a change in the color tone etc. of each composition after preservation at 80° C. for 2 days and the residual ratio of the phosphatidylcholine after preservation at 80° C. for 2 days) was performed as described in Test Example 1, and a test for evaluating the transdermal absorption of the phosphatidylcholine and a test for evaluating the transdermal absorption of the L-carnitine were performed as described in Test Example 2. The results are summarized and shown in Table 2.

positively correlated. From these results, it was presumed that a cluster ion having a constant composition consisting of the phosphatidylcholine and L-carnitine was formed in the external composition of the present invention, and it was presumed that the positive correlation was observed since the cluster ion contributed to the skin passage.

For example, as shown in No. 2, the L-carnitine aqueous solution is added to, and homogeneously dispersed in, the propylene glycol/glycerin solution of the phosphatidylcholine to give an external composition in which phosphatidyl-

TABLE 2

| | Test Item | Reference Example 2 | Reference Example 3 | No. 1 | No. 2 | No. 3 | No. 4 |
|---|---|---|---|---|---|---|---|
| Stability Test | Change in Color Tone and the Like of Composition after Preservation at 80° C. for 2 Days | change in color | change in color and white turbidity | No Particular Change | No Particular Change | No Particular Change | No Particular Change |
| | Residual Ratio of Phosphatidylcholine after Preservation at 80° C. for 2 Days | 74.7% | 91.7% | 97.7% | 97.4% | 97.3% | 97.4% |
| Transdermal Absorbability Test | Residual Ratio of Phosphatidylcholine in Composition: after 5 Hours of Application | 98.7% | 100.5% | 63.7% | 59.8% | 54.9% | 59.2% |
| | Residual Ratio of L-Carnitine In Composition: after 5 Hours of Application | — | — | 68.0% | 61.7% | 51.3% | 60.9% |

[Note]
—: Not Measured because of No Addition of Carnitine

When Nos. 1 to 4 of the present invention were compared with Reference Examples 1 to 2 which are free from L-carnitine, stability and transdermal absorbability of phosphatidylcholine exerted by Nos. 1 to 4 of the present invention were much greater.

Particularly, significant differences were observed in the transdermal absorbability. In the case of the compositions which are free from L-carnitine (Reference Examples 1 to 2), data was obtained, from which it can be considered that the phosphatidylcholine is almost not delivered into the skin.

choline micelles are dispersed as colloido. The colloidal particles of the present invention had an average particle diameter (d50) of 366 nm as shown in FIG. 2. The stability of the phosphatidylcholine in the composition of the present invention was 97.4% after preservation at 80° C. for 2 days, and no coloration was observed. As described above, the cluster ion of the phosphatidylcholine and L-carnitine was formed to be stable and probably contribute to the sufficient stability of the phosphatidylcholine and L-carnitine. In addition, regarding the transdermal absorption, back calculation from the residual ratio after 5 hours of application demonstrated that about 40% of the phosphatidylcholine in the composition migrated into the skin and about 40% of the carnitine migrated into the skin, as shown in Example 2.

Figure 1:
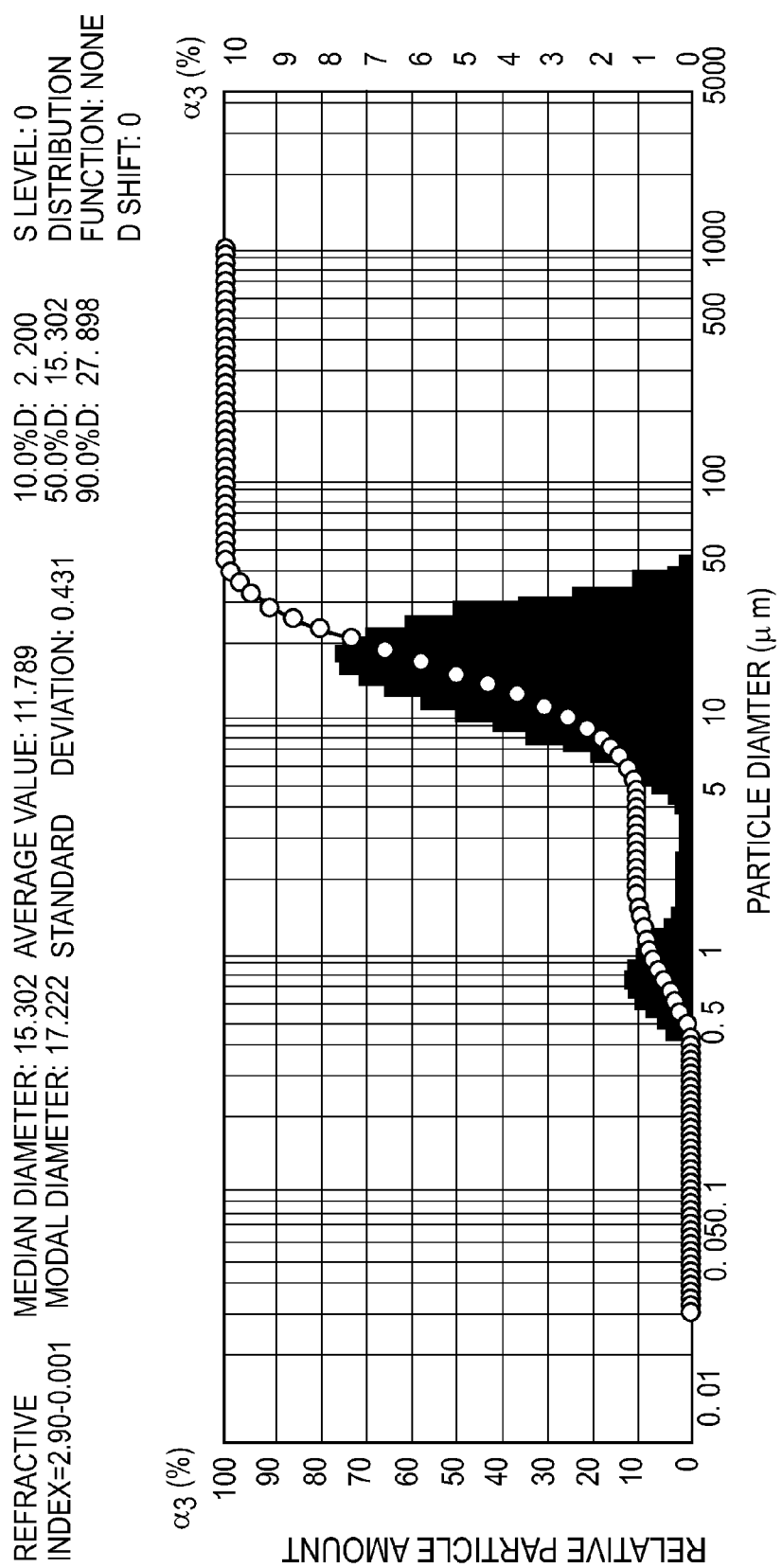
FIG. 1 is a graph showing the particle diameter of colloidal particles in the external composition according to Reference Example 2, where the composition is free from L-carnitine.

The particle diameter (d50) of colloidal particles in the external composition which is free from L-carnitine like Reference Example 1 is about 15.3 μm as shown in FIG. 1. This particle diameter was about 42-fold larger compared to the particle diameter of colloidal particles in No. 1.

As described above, it was demonstrated that the stability and transdermal absorbability of the phosphatidylcholine were influenced by the formation of a cluster ion and the particle diameter of colloidal particles. It was clear that there is a tendency that formation of a cluster ion increases the stability of the phosphatidylcholine and smaller particle diameter enhances transdermal absorption of phosphatidylcholine.

Test Example 1

Test for Evaluating Stability of Phosphatidylcholine

A container made of an aluminum-laminated film was filled with test solutions of Nos. 1 to 4 of Example 1 and test solutions of Reference Examples 1 to 2, followed by heat-sealing, and preserved in an incubator at 80° C. for 2 days. After preservation, the color tone of each test solution was observed; and about 0.5 g of the test solution was taken, followed by addition of 10 mL of methanol and sonication, and the content of the residual phosphatidylcholine was determined by HPLC. The results were compared with the content which was separately measured before the incubation at 80° C. to calculate the residual ratio (%).

These results are described in Table 2.

Test Example 2

Test for Transdermal Absorption of Phosphatidylcholine and L-Carnitine

Gauzes having a diameter of 2 cm (a quadruple ply) were immersed in about 1.2 g of each of test solutions of Nos. 1 to 4 of Example 1 and test solutions of Reference Examples 1 to 2. The obtained gauzes were applied to the arm of healthy volunteers, covered with a plastic film, and then continued to be applied for 5 hours. After the end of application, the gauzes and the plastic film (A) were recovered; the applied site was wiped off three times with a dry gauze, once with a gauze wrung out with warm water, and further once with a dry gauze; then, these gauzes were combined with the recovered (A), followed by addition of 30 mL of methanol and sonication; and the contents of the remaining phosphatidylcholine and L-carnitine were measured by HPLC. The results were compared with the content which was separately measured before application to calculate the residual ratio (%).

These results are described in Table 2 above.

Example 2

Effect of Quantitative Ratio of Phosphatidylcholine and L-Carnitine

To examine the influence of the composition content (molar ratio) of a cluster ion formed mainly by a phosphatidylcholine and a carnitine, each reagent was weighed so that the transdermal composition having composition ratio (w/w %) listed in Table 3 below was prepared, like Example 1. The average particle diameter of colloidal particles was measured using Zetasizer Nano from Malvern Co., Ltd. The results are summarized and described in Table 3 below.

TABLE 3

| Reagent | No. 5 | No. 2 | No. 6 |
|---|---|---|---|
| Egg Yolk High-Purity Phosphatidylcholine (Mw 732~790) | 2.0 (2.5-2.7 mM) | 2.0 (2.5-2.7 mM) | 2.0 (2.5-2.7 mM) |
| L-Carnitine (Mw 161.2) | 0.5 (3.1 mM) | 2.0 (12.4 mM) | 5.0 (31.0 mM) |
| Propylene Glycol | 23 | 22 | 26 |
| Glycerin | 23 | 22 | 22 |
| Water | 43 | 43 | 37 |
| Ethanol | 8.5 | 9 | 8 |
| pH Adjuster (Citric Acid) | Appropriate Amount | Appropriate Amount | Appropriate Amount |
| Property of liquid (pH) | 5 | 5 | 5 |
| Stability Test Residual Ratio of Phosphatidylcholine after Preservation at 80° C. for 2 Days | 97.2% | 97.4% | 98.0% |
| Residual Ratio of Phosphatidylcholine after 5 Hours of Application | 57.8% | 59.8% | 51.9% |
| Average Particle Diameter of Colloidal Particle | 106 nm | 106 nm | 80 nm |

As shown in Table 3, it was found that when the amount of the carnitine was equal to or exceeded the equimolar amount of the phosphatidylcholine, the average particle diameter of the colloidal particles reached about 100 nm. In addition, it was shown that there was tendency that the increased amount of the carnitine decreases the average particle diameter.

It was also shown that the decreased average particle diameter of the colloidal particles enhanced the transdermal absorption of the phosphatidylcholine.

Example 3

Effect of Addition of Ethanol as Fragrance

To evaluate the influence of ethanol as a monohydric alcohol and a fragrance, each reagent was weighed so that a transdermal composition having the composition ratio (w/w %) listed in Table 4 below was prepared, like Example 1. The average particle diameter of colloidal particles was evaluated like Example 2; the results are shown in Table 4.

TABLE 4

| Reagent | No. 2 | No. 7 |
|---|---|---|
| Egg Yolk High-Purity Phosphatidylcholine (Mw 732~790) | 2.0 (2.5-2.7 mM) | 2.0 (2.5-2.7 mM) |
| L-Carnitine (Mw 161.2) | 2.0 (12.4 mM) | 2.0 (12.4 mM) |
| Propylene Glycol | 22 | 24.3 |
| Glycerin | 22 | 24.3 |
| Water | 43 | 47.4 |
| Ethanol | 9 | 0 |
| pH Adjuster (Citric Acid) | Appropriate Amount | Appropriate Amount |
| Property of liquid (pH) | 5 | 5 |

TABLE 4-continued

| Reagent | No. 2 | No. 7 |
|---|---|---|
| Stability Test Residual Ratio of Phosphatidylcholine after Preservation at 80° C. for 2 Days | 97.4% | 98.1% |
| Residual Ratio of Phosphatidylcholine after 5 Hours of Application | 59.8% | 56.5% |
| Average Particle Diameter of Colloidal Particle | 106 | 96 |

Table 4 above showed that the stability of the phosphatidylcholine, the transdermal absorbability of the phosphatidylcholine and the average particle diameter of colloidal particles were little influenced by the presence or absence of ethanol as the monohydric alcohol.

Example 4

Effect of Forced Stirring on Average Particle Diameter of Colloidal Particle

To determine the influence of stirring on the miniaturization of colloidal particles (conversion into nanoparticles), each reagent was weighed so that a transdermal composition having the composition ratio (w/w %) listed in Table 5 below was prepared, like Example 1. After preparing the composition, to determine the effect of stirring on the average particle diameter, the effect of forced stirring at a rotating speed of 3,000 rpm was examined. The results are summarized and described in Table 5.

TABLE 5

| Reagent | No. 2 | No. 8 |
|---|---|---|
| Egg Yolk High-Purity Phosphatidylcholine (Mw 732~790) | 2.0 (2.5-2.7 mM) | 4.0 (5.0-5.4 mM) |
| L-Carnitine (Mw 161.2) | 2.0 (12.4 mM) | 4.0 (24.8 mM) |
| Propylene Glycol | 22 | 2 |
| Glycerin | 22 | 22 |
| Water | 43 | 39 |
| Ethanol | 9 | 9 |
| pH Adjuster (Citric Acid) | Appropriate Amount | Appropriate Amount |
| Property of liquid (pH) | 5 | 5 |
| Forced Stirring (3000 rpm) | Not conducting | 50 min |
| Average Particle Diameter of Colloidal Particle | 106 | 115 |

Table 5 above showed that the average particle diameter of the colloidal particles was not quite influenced by the presence or absence of the forced stirring. In general, forced stirring over time tends to make the colloidal particles finer. However, in the case of the present invention, it appears that forced stirring over time does not have so great effect on the miniaturization of the colloidal particles.

Test Example 3

Evaluation of Average Particle Diameter of Colloidal Particle a) Method of Measuring Particle Size using Laser Diffraction Techniques:

Sample No. 2 of Example 1 and the sample of Reference Example 2 were each diluted by 10-fold with water, dispersed using an ultrasonic wave, and then subjected to measurement. The average particle diameter (d50) of colloidal particles was measured using SALD-2200 from Shimadzu Corporation as a measuring apparatus.

b) Method of Measuring Particle Size using Dynamic Light Scattering Techniques:

The sample of each number of Examples 1 to 4 was directly subjected to measurement without dilution. The average particle diameter of colloidal particles was measured using Zetasizer Nano from Malvern Co., Ltd. as a measuring apparatus.

INDUSTRIAL APPLICABILITY

The transdermal composition of the present invention is a preparation in which a lipophilic base (a fat and oil) or a surfactant is not used, and which allows phosphatidylcholine to be stably dispersed as colloidal particles in an aqueous solution comprising only a hydrophilic base due to the effect of L-carnitine. Thus, the transdermal composition of the present invention is kind to the skin and adaptable to the skin. Therefore, the preparation of the present invention can be suitably used as a transdermal preparation for external use and a cosmetic for removing or reducing the subcutaneous accumulation of fat at a desired site.

The invention claimed is:

1. A transdermal composition consisting of phosphatidylcholine derived from a natural product, L-carnitine, propylene glycol, glycerin, water, and optionally, one or more selected from the group consisting of a fragrance, an antioxidant, a preservative, a colorant, a buffer, a pH adjuster, an ultraviolet absorber, and an antimicrobial agent.

2. The transdermal composition according to claim 1, wherein the phosphatidylcholine is egg yolk phosphatidylcholine or soybean phosphatidylcholine.

3. The transdermal composition according to claim 1, wherein the phosphatidylcholine is dispersed as a colloidal dispersion in a solution of the transdermal composition.

4. The transdermal composition according to claim 1, wherein the total content of the phosphatidylcholine and L-carnitine is 1 to 16 w/w %.

5. The transdermal composition according to claim 1, wherein said fragrance is present.

6. The transdermal composition according to claim 5, wherein said fragrance is ethanol.

7. The transdermal composition according to claim 2, wherein the phosphatidylcholine is dispersed as a colloidal dispersion in a solution of the transdermal composition.

8. The transdermal composition according to claim 1, wherein the content of phosphatidylcholine is 1 to 6 w/w %.

9. The transdermal composition according to claim 1, wherein the mole ratio of L-carnitine to phosphatidylcholine is 4:1 to 10:1.

10. The transdermal composition according to claim 1, wherein the weight ratio of glycerin to propylene glycol is 0.2:1 to 3:1.

11. The transdermal composition according to claim 1, wherein the natural product-derived phosphatidylcholine and the L-carnitine form a cluster ion.

12. The transdermal composition according to claim 2, wherein the natural product-derived phosphatidylcholine and the L-carnitine form a cluster ion.

13. The transdermal composition according to claim 1, wherein the phosphatidylcholine is dispersed as colloidal particles of about 100 nm or less in a solution of the transdermal composition.

14. The transdermal composition according to claim 2, wherein the phosphatidylcholine is dispersed as colloidal particles of about 100 nm or less in a solution of the transdermal composition.

* * * * *